US012409610B2

(12) United States Patent
Arima et al.

(10) Patent No.: US 12,409,610 B2
(45) Date of Patent: Sep. 9, 2025

(54) APPARATUS AND METHOD FOR ULTRASONIC WELDING

(71) Applicant: ZUIKO CORPORATION, Osaka (JP)

(72) Inventors: Takashi Arima, Osaka (JP); Masato Hiroyasu, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 70 days.

(21) Appl. No.: 18/033,594

(22) PCT Filed: Oct. 12, 2021

(86) PCT No.: PCT/JP2021/037664
§ 371 (c)(1),
(2) Date: Apr. 25, 2023

(87) PCT Pub. No.: WO2022/102317
PCT Pub. Date: May 19, 2022

(65) Prior Publication Data
US 2023/0398747 A1    Dec. 14, 2023

(30) Foreign Application Priority Data
Nov. 13, 2020   (JP) ................. 2020-189438

(51) Int. Cl.
*B29C 65/08*      (2006.01)
*A61F 13/15*      (2006.01)
*A61F 13/496*     (2006.01)
*B29C 65/00*      (2006.01)
*B29L 31/48*      (2006.01)

(52) U.S. Cl.
CPC ........ *B29C 65/08* (2013.01); *A61F 13/15739* (2013.01); *B29C 66/8322* (2013.01); *B29C 66/83411* (2013.01); *B29C 66/951* (2013.01); *A61F 2013/15869* (2013.01); *B29L 2031/4878* (2013.01)

(58) Field of Classification Search
CPC ........... A61F 2013/15869; A61F 13/49; B29C 65/086
See application file for complete search history.

(56) References Cited

U.S. PATENT DOCUMENTS

| 5,660,679 A | 8/1997 | Rajala et al. |
| 2013/0174965 A1 | 7/2013 | Yamamoto et al. |
| 2016/0107377 A1* | 4/2016 | Fujita ................. B29C 66/8322 156/580.2 |

(Continued)

FOREIGN PATENT DOCUMENTS

| EP | 3 092 994 A1 | 11/2016 |
| EP | 3092993 A1 * | 11/2016 |

(Continued)

OTHER PUBLICATIONS

International Search Report for corresponding Application No. PCT/JP2021/037664, mailed Jan. 11, 2022.

*Primary Examiner* — Jeffry H Aftergut
(74) *Attorney, Agent, or Firm* — Renner, Otto, Boisselle & Sklar, LLP

(57) ABSTRACT

A control is performed to drive a horn via an ultrasonic wave generator so as to apply ultrasonic energy to a web in one of an outward path and a return path of an anvil and not to apply ultrasonic energy to the web in the other one of the outward path and the return path.

4 Claims, 10 Drawing Sheets

(56) References Cited

U.S. PATENT DOCUMENTS

2017/0027762 A1    2/2017  Fujita et al.

FOREIGN PATENT DOCUMENTS

| EP | 3092995 A1 | * | 11/2016 |
| JP | 3988835 B2 | | 10/2007 |
| JP | 2012-076343 A | | 4/2012 |
| JP | 2015-130938 A | | 7/2015 |
| JP | 2015-130939 A | | 7/2015 |
| JP | 6228232 B2 | | 11/2017 |

* cited by examiner

APPARATUS AND METHOD FOR ULTRASONIC WELDING

TECHNICAL FIELD

The present invention relates to a device and a method for ultrasonic welding.

BACKGROUND ART

A device having a horn that rotates together with a drum and an anvil that cooperates with the horn has been known in the art, in which the anvil reciprocates in the axial direction of the drum as the drum rotates so as to perform a welding process on a web held between the horn and the anvil (the first patent document).

CITATION LIST

Patent Document

[FIRST PATENT DOCUMENT] Japanese Patent No. 6228232 (Abstract)

SUMMARY OF INVENTION

With this prior art, the welding process is performed in both of the reciprocating movements of the anvil, but there have been problems such as unstable welding strength and deteriorated appearance due to misalignment between the weld trace of the outward path and the weld trace of the return path caused by the web being misaligned while the anvil reciprocates.

Therefore, an object of the present invention is to provide a device and a method for ultrasonic welding capable of realizing stable weld strength and forming a weld trace of excellent appearance.

An ultrasonic welding device of the present invention includes:
- a conveying drum 200 that conveys a web W along an outer circumferential surface 44a of the drum 200 while rotating;
- at least one horn 14 that is arranged on one of an inner side and an outer side in a radial direction of the conveying drum 200 relative to the outer circumferential surface 44a, and that rotates together with the conveying drum 200;
- at least one anvil 15 that is arranged on the other one of the inner side and the outer side in the radial direction of the conveying drum 200 relative to the outer circumferential surface 44a, and that rotates together with the conveying drum 200;
- a moving mechanism 300 that reciprocates the anvil 15 in an axis L1 direction of the conveying drum 200 as the conveying drum 200 rotates so as to hold the web W between the anvil 15 and the horn 14 in an outward path OB and a return path IB of the anvil 15;
- an ultrasonic wave generator 16 that vibrates the horn 14 to apply ultrasonic energy to the web W sandwiched between the anvil 15 and the horn 14; and
- a control unit 500 that performs a control of vibrating the horn 14 via the ultrasonic wave generator 16 so as to apply ultrasonic energy to the web W in one of the outward path OB and the return path IB and (whereas) not to apply ultrasonic energy to the web W in the other one of the outward path OB and the return path IB.

On the other hand, an ultrasonic welding method of the present invention is an ultrasonic welding method of welding a web W by means of an ultrasonic welding device, the ultrasonic welding device including:
- a conveying drum 200 that conveys the web W along an outer circumferential surface 44a of the drum 200 while rotating;
- at least one horn 14 that is arranged on one of an inner side and an outer side in a radial direction of the conveying drum 200 relative to the outer circumferential surface 44a, and that rotates together with the conveying drum 200; and
- at least one anvil 15 that is arranged on the other one of the inner side and the outer side in the radial direction of the conveying drum 200 relative to the outer circumferential surface 44a, and that rotates together with the conveying drum 200; the ultrasonic welding method including:
- a step of conveying the web W by the conveying drum 200;
- a step of reciprocating the anvil 15 in an axis L1 direction of the conveying drum 200 as the conveying drum 200 rotates so as to hold the web W between the anvil 15 and the horn 14 in an outward path OB and a return path IB of the anvil 15
- a step of vibrating the horn 14 to apply ultrasonic energy to the web W sandwiched between the anvil 15 and the horn 14; and
- a step of controlling vibration of the horn 14 via an ultrasonic wave generator 16 so as to apply ultrasonic energy to the web W in one of the outward path OB and the return path IB and (whereas) not to apply ultrasonic energy to the web W in another one of the outward path OB and the return path IB.

According to the present invention, the web is welded only in one of the outward path and the return path. Therefore, there will not be misalignment between weld traces, the welding strength will not be unstable, and the appearance will not deteriorate.

As used in the present invention, "to weld a web" may be to weld together a plurality of webs that are laid on each other or may be to weld a single layered web folded in two, i.e., so-called side sealing.

DESCRIPTION OF EMBODIMENTS

Figure 1:
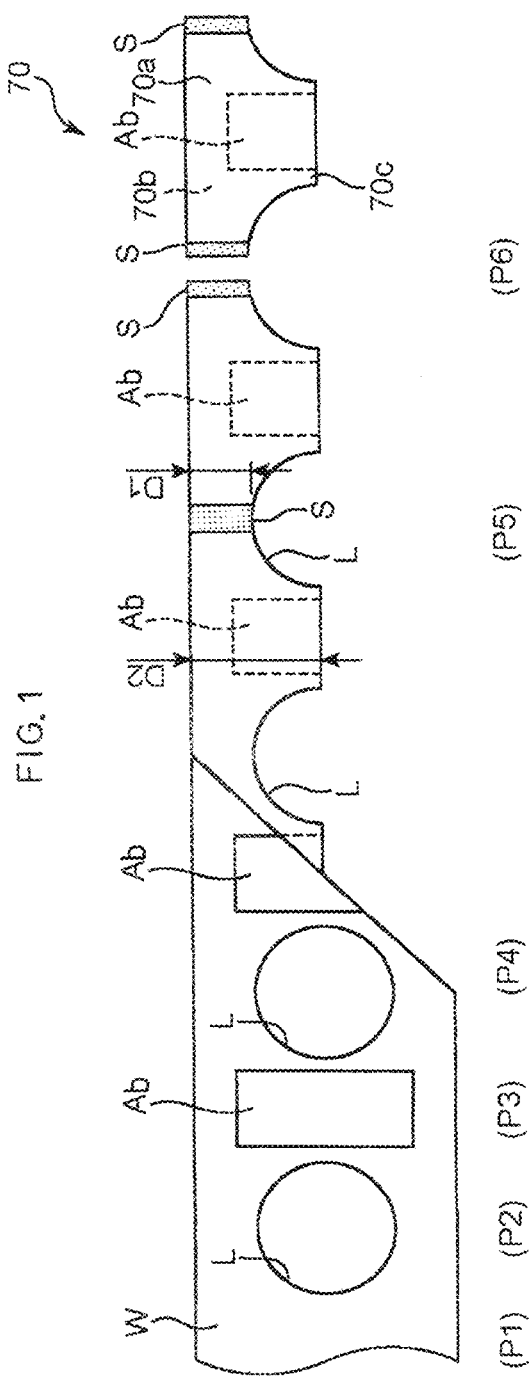
FIG. 1 is a process diagram illustrating the outline of a method for manufacturing a disposable diaper according to the present invention.

Preferably, in the present invention, the control unit 500 controls the ultrasonic wave generator 16 so as not to vibrate the horn 14 when ultrasonic energy is not applied to the web W.

In this case, it is possible to suppress generation of unnecessary vibration to the web W being conveyed.

Preferably, in the present invention, the moving mechanism 300 is configured so that the anvil 15 reciprocates so that an average moving velocity of the anvil 15 in the one of the outward path OB and the return path IB in which ultrasonic energy is applied is smaller than that in the other one of the outward path OB and the return path IB.

In this case, it is possible to sufficiently weld the web because the moving velocity of the anvil in the one path is small, while the amount of time taken for reciprocation of the anvil required for a welding process will not be large because the moving velocity of the anvil in the other path is large.

Preferably, in the present invention, the moving mechanism 300 is configured so that the anvil 15 overruns beyond a welding area α where the web W should be welded.

in this case, ultrasonic welding can be performed on the web over the entire range in a direction that intersects with the conveyance direction of the web.

Preferably, in the present invention, the control unit 500 controls the ultrasonic wave generator 16 so as not to vibrate the horn 14 in the overrun area β.

In this case, it is possible to prevent damage due to contact between the anvil and the horn.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Before describing a device according to the present invention, the structure of a disposable diaper 70, which is an example product manufactured by the device, and the manufacturing method thereof will be described.

Referring to FIG. 1, the disposable diaper 70 includes a front abdomen portion 70*a* which, when worn, is arranged on the abdomen of the wearer, a rear back portion 70*b* which is positioned on the buttocks of the wearer, and a crotch portion 70*c* which extends from the front abdomen portion 70*a* through between both legs of the wearer to the rear back portion 70*b*.

The opposite side edge portions of the front abdomen portion 70*a* and the opposite side edge portions of the rear back portion 70*b* are welded to each other by two welded portions S so that the front abdomen portion 70*a* and the rear back portion 70*b* are linked together into a ring form.

The outline of the method for manufacturing the disposable diaper 70 will now be described.

<Conveying Step P1>

In the conveying step P1, a web W extending in a particular direction is conveyed along its longitudinal direction. The flow direction of the web W will be hereinafter described as the horizontal direction, and the direction orthogonal to the horizontal direction in FIG. 1 as the vertical direction.

The web W includes an inner web that faces toward the body surface of the wearer when worn, an outer web that faces away from the wearer when worn, and elastic members sandwiched between the inner web and the outer web. Note that the inner web, the outer web and the elastic members are not shown in the figures.

<Leg Hole Formation Step P2>

In the leg hole formation step P2, leg holes L are formed at the center position in the vertical direction of the web W.

The area between two leg holes L in the web W is a portion that corresponds to the crotch portion 70*c*. The opposite positions in the vertical direction relative to the portion that corresponds to a crotch portion 70*c* in the web W are portions that correspond respectively to the front abdomen portion 70*a* and the rear back portion 70*b*.

<Absorbent Body Attachment Step P3>

In the absorbent body attachment step P3, an absorbent body Ab is attached to a position between two leg holes L on the web W.

The absorbent body Ab includes a permeable sheet having liquid permeability, a water-repellent sheet having water repellency and air permeability, and an absorbent core sandwiched between the permeable sheet and the water-repellent sheet. Note that the permeable sheet, the water-repellent sheet and the absorbent core are not shown in the figures.

Note that although the method for attaching the absorbent body Ab on the web W is described, the attachment may be done with the absorbent core sandwiched between the inner web and the outer web of the web W. In this case, the inner web is formed of a liquid-permeable sheet, and the outer web is formed of a water-repellent and air-permeable sheet.

<Two-Fold Step P4>

In the two-fold step P4, the web W on which the absorbent body Ab is placed is folded in two in the vertical direction. Thus, a portion of the web W that corresponds to the front abdomen portion 70*a* and a portion thereof that corresponds to the rear back portion 70*b* are laid on each other.

<Welding Step P5>

In the welding step P5, a portion of the two-folded web W (the object to be welded) that corresponds to the side edge portion of the front abdomen portion 70*a* and a portion thereof that corresponds to the side edge portion of the rear back portion 70*b* are ultrasonically welded to each other between two absorbent bodies Ab adjacent to each other.

Specifically, in the welding step P5, the web W is ultrasonically welded over a range that includes the position at which the web W is severed in the cut-off step P6 to be described below. Thus, side sealing is done, making the torso portion of the worn article into a loop, thereby turning the diaper into a pants-type diaper.

Note that the welded portions S are formed over a welding range D1 in the vertical direction respectively for a portion that corresponds to the side edge portion of the front abdomen portion and for a portion that corresponds to the side edge portion of the rear back portion 70*b*.

<Cut-Off Step P6>

In the cut-off step P6, the web W is cut off along the cut-off line extending in the vertical direction at the center position of the welded portion S formed in the welding step P5. Thus, the web W (continuous material) is cut off into disposable diapers 70.

Next, the outline of the ultrasonic welding device 1 according to the present invention will be described.

Figure 2:
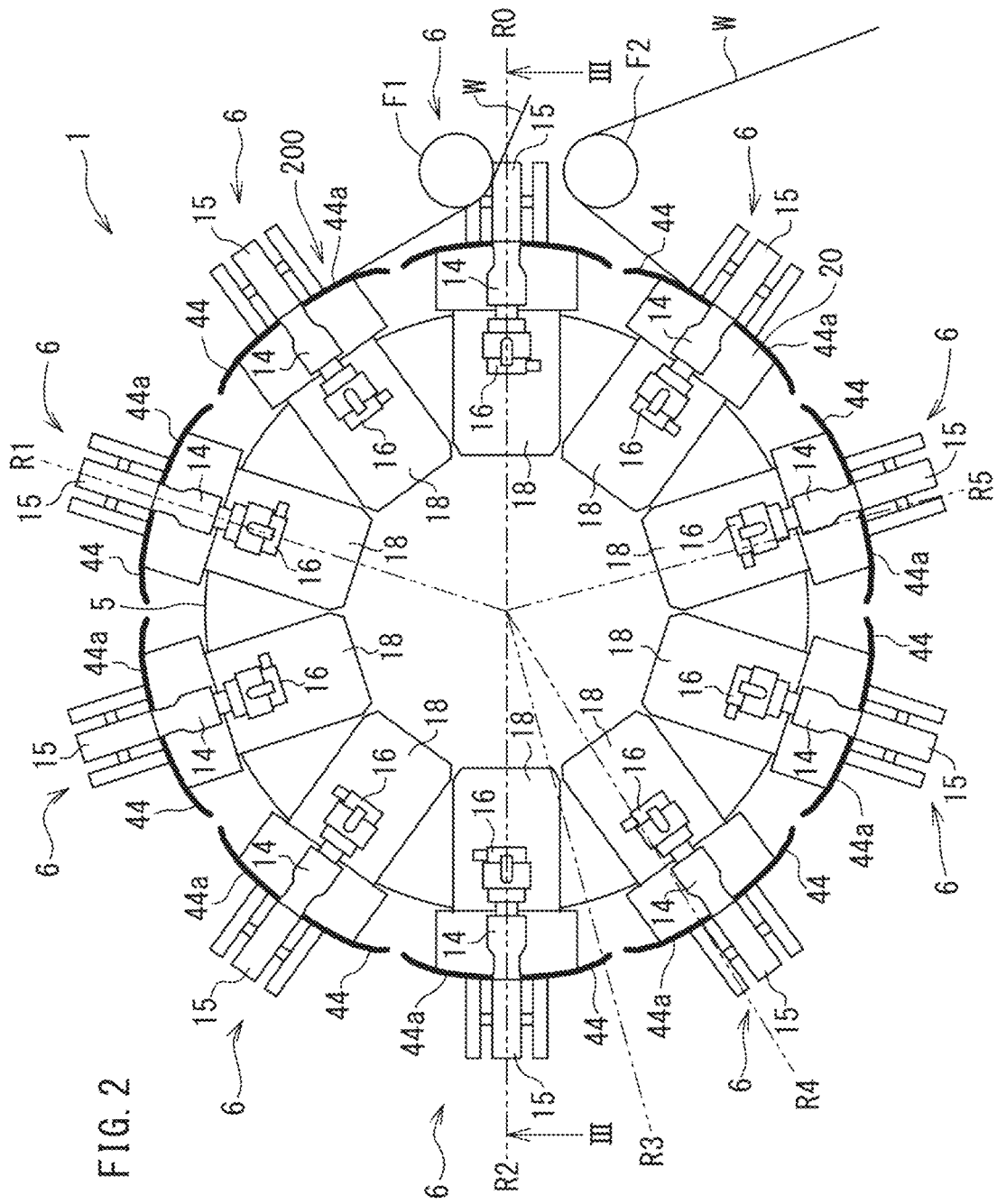
FIG. 2 is a front view of a main part of an ultrasonic welding device according to the present invention.

As shown in FIG. 2, the ultrasonic welding device 1 includes a conveying drum 200 which rotates and conveys the web W along the outer circumferential surface 44a in the circumferential direction.

Note that the circumferential velocity of the conveying drum 200 and the conveying velocity of the web W are set to be equal to each other so that the web W does not slip on the outer circumferential surface 44a.

The conveying drum 200 includes a horn 14, which is arranged on the inner side in the radial direction of the conveying drum 200 relative to the outer circumferential surface 44a, and rotates together with the conveying drum 200.

The conveying drum 200 includes an anvil 15, which is arranged on the outer side in the radial direction of the conveying drum 200 relative to the outer circumferential surface 44a, and rotates together with the conveying drum 200.

In this example, ten horns 14 and ten anvils 15 are provided.

Figure 4:
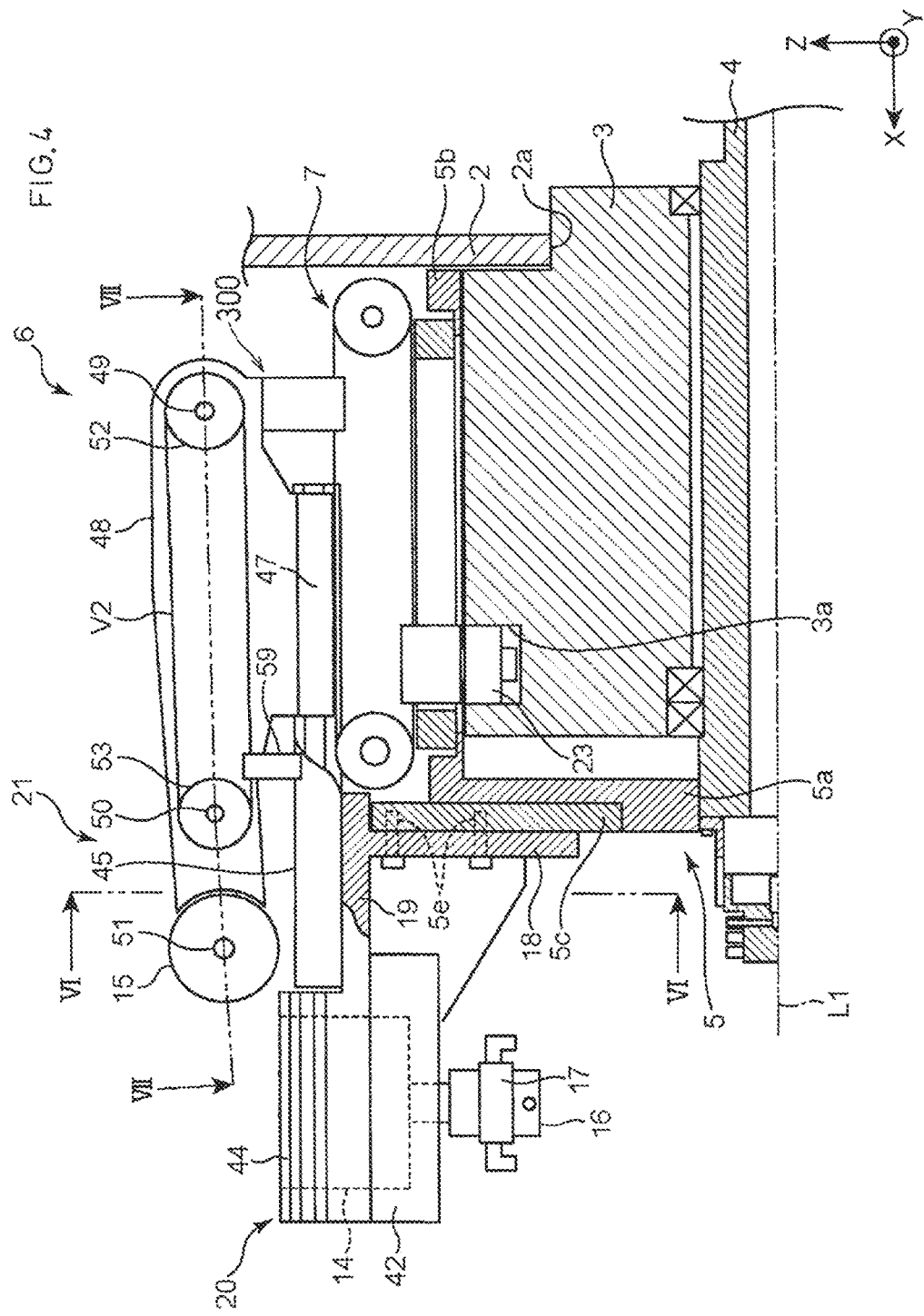
FIG. 4 is a cross-sectional view showing a part of FIG. 3 on an enlarged scale.

The moving mechanism 300 of FIG. 4 reciprocates the anvil 15 in the axis L1 direction of the conveying drum 200 as the conveying drum 200 rotates.

As will be described below, the web W (FIG. 2) is held between the anvil 15 and the horn 14 in the outward path and the return path of the anvil 15.

Figure 7:
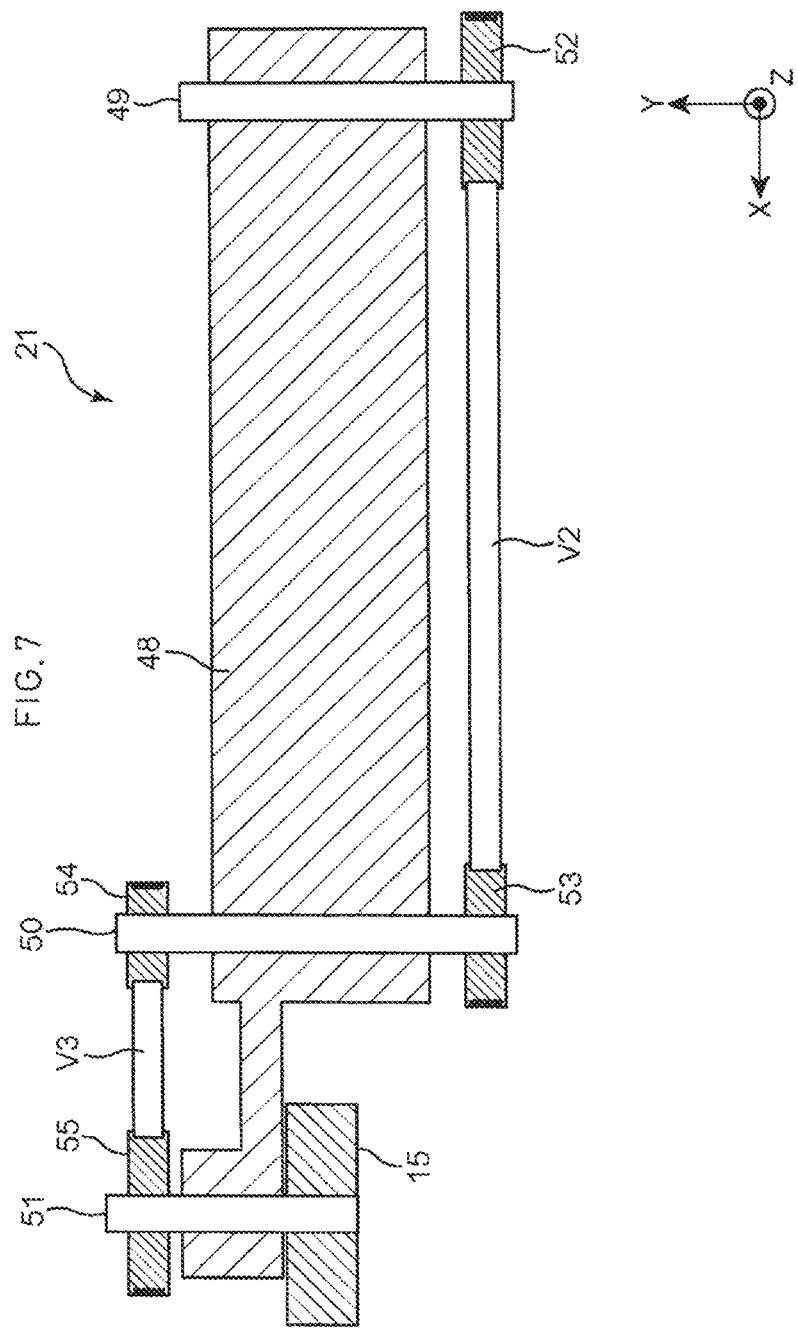
FIG. 7 is cross-sectional view taken along line FIG. 4.

Note that the web W is not shown in to FIG. 7.

An ultrasonic wave generator 16 of FIG. 2 is provided for each horn 14 and vibrates the horn 14 to apply ultrasonic energy to the web W sandwiched between the anvil 15 and the horn 14. The horn 14 vibrates, for example, in a direction that intersects with the surface of the web W.

Figure 3:
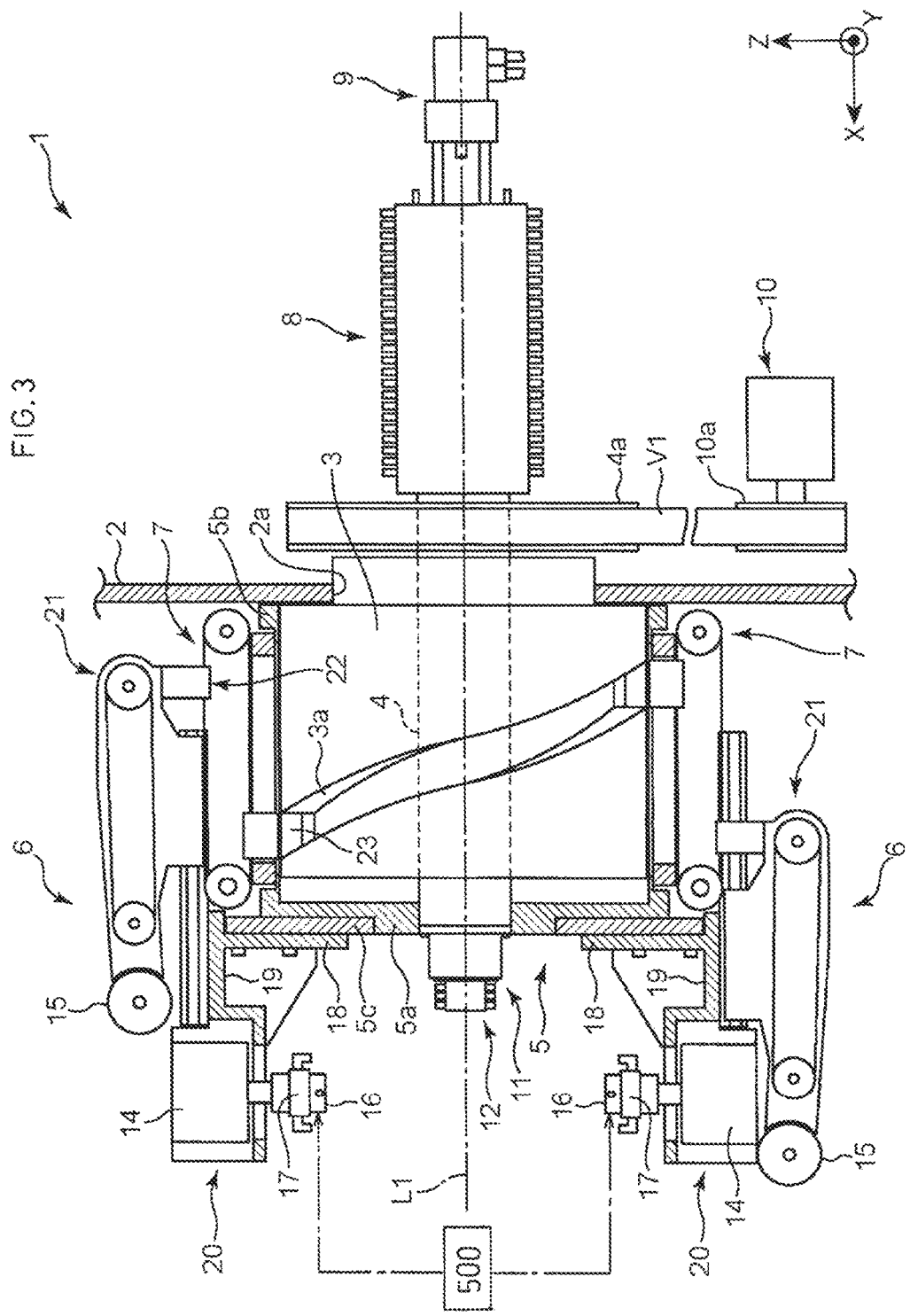
FIG. 3 is a cross-sectional view taken along line III-III of FIG. 2.

The control unit 500 of FIG. 3 performs a control of vibrating the horn 14 via the ultrasonic wave generator 16 so as to apply ultrasonic energy to the web W in either one of the outward path and the return path and not to apply ultrasonic energy to the web W in the other one of the outward path OB and the return path IB.

The control unit 500 in this example controls the ultrasonic wave generator 16 so as to apply ultrasonic energy to the web W in the outward path OB and not to apply ultrasonic energy to the web W in the return path IB.

Note that "not apply ultrasonic energy" as used in the present specification includes the case where the horn is vibrating to such an extent that the web is not welded.

Next, referring to FIG. 2, the ultrasonic welding device 1 performing the welding step P5 will be described in detail.

The ultrasonic welding device 1 is for ultrasonically welding the web W, which has been folded in two in the two-fold step P4 and introduced via an inlet roller F1, and to send the welded web W to the cut-off step P6 via an outlet roller F2.

Specifically, as shown in FIG. 3, the ultrasonic welding device 1 includes: a drive shaft support member 2 provided upright on a predetermined work surface; a cam drum (drive mechanism) 3 fixed to the drive shaft support member 2; a cam follower (drive mechanism) 23 provided in a cam groove 3a of the cam drum 3; a drive shaft 4 supported so that the drive shaft 4 can rotate relative to the drive shaft support member 2 about the axis L1; a rotating drum 5 fixed to the drive shaft 4; ten welding units 6 fixed to the rotating drum 5; ten power transmission mechanisms 7 (only two are shown in FIG. 3) for transmitting power from the cam drum 3 and the cam follower 23 to the welding unit 6; a slip ring (rotary connector) 8 and a rotary joint 9 provided at the proximal portion of the drive shaft 4; a wire guide member 11 and a pipe connection member 12 provided at the distal portion of the drive shaft 4; and a motor 10 for rotationally driving the drive shaft 4.

Note that in FIG. 3, the X direction is the direction parallel to the axis L1 of the drive shaft 4, the Z direction is the up-down direction of FIG. 3, the Y direction is the direction orthogonal to the X-Z plane.

Referring to FIG. 3 and FIG. 4, the drive shaft support member 2 supports the elements described above (excluding the drive shaft support member 2) of the ultrasonic welding device 1 on the work surface. Specifically, the drive shaft support member 2 is a plate-shaped member with a through hole 2a passing through the drive shaft support member 2 in the X direction.

The cam drum 3 is fixed to the drive shaft support member 2 with one end thereof in the X direction fitted into the through hole 2a of the drive shaft support member 2. In this state, the axis of the cam drum 3 is aligned with the axis L1.

The cam groove 3a is formed on the outer circumferential surface of the cam drum 3. The cam groove 3a has a shape that permits the cam follower 23, which rotates about the axis L1, to move in the X direction, as will be described in detail below. Note that the cam drum 3 and the cam follower 23 correspond to the drive mechanism for driving the anvil 15 to be described below so that the anvil 15 moves relative to the horn 14.

As shown in FIG. 3, the drive shaft 4 is rotationally driven by the motor 10. Specifically, a belt V1 is wound around a pulley 4a provided at a middle portion of the drive shaft 4 and a pulley 10a provided on the output shaft of the motor 10. The power of the motor 10 is transmitted to the drive shaft 4 via the belt V1 as the output shaft of the motor 10 rotates. Note that the motor 10 is fixed to the drive shaft support member 2 via a bracket (not shown).

The drive shaft 4 passes through the cam drum 3 in the X direction in such a state that the drive shaft 4 can rotate relative to the cam drum 3. That is, the drive shaft 4 is supported indirectly by the drive shaft support member 2 via the cam drum 3. The proximal portion of the drive shaft 4 is located on the opposite side of the drive shaft support member 2 from the cam drum 3, and the distal portion of the drive shaft 4 is located on the opposite side of the cam drum 3 from the drive shaft support member 2.

The rotating drum 5 includes a disc 5a fixed to the distal portion of the drive shaft 4, a covering wall a extending in the X direction from the peripheral portion of the disc 5a and covering the outer circumferential surface of the cam drum 3, and an adjustment plate 5c removably attached to the opposite side of the disc 5a from the covering wall 5b. Note that the disc 5a and the adjustment plate 5c correspond to a rotor capable of rotating about the axis L1.

The adjustment plate 5c has screw holes 5e (see FIG. 4) for attaching the welding unit 6.

The welding unit 6 including the horn 14 and the anvil 15 will now be described with reference to FIG. 4 to FIG. 7. Note that since ten welding units 6 have an identical configuration, only the configuration of one welding unit 6 shown in FIG. 4 to FIG. 7 will be described.

The welding unit 6 includes: the horn (second welder) 14 and the anvil (first welder) 15 for welding the web W by sandwiching the web W therebetween; the ultrasonic wave generator 16 connected to the horn 14; a cooling jacket 17 (cooler) for cooling the ultrasonic wave generator 16; an attachment portion 18 that permits the welding unit 6 to be attached to the rotating drum 5 (the adjustment plate 5*c*); a base 19 linked to an end portion of the attachment portion 18 and extending in the X direction; a horn holding mechanism 20 provided at the distal portion of the base 19 for holding the horn 14; and an anvil holding mechanism 21 provided at the proximal portion of the base 19 for holding the anvil 15.

The attachment portion 18 permits the welding unit 6 to be attached to the rotating drum 5 with the horn holding mechanisms 20 being arranged on an identical circumference about the axis L1 as shown in FIG. 2 and FIG. 3. Moreover, the attachment portion 18 can be attached to the rotating drum 5 (the adjustment plate 5*c*) so that the attachment position of the welded unit 6 to the rotating drum 5 can be adjusted in the radial direction about the axis L1 (in the Z direction in FIG. 4 to FIG. 6).

Figure 5:
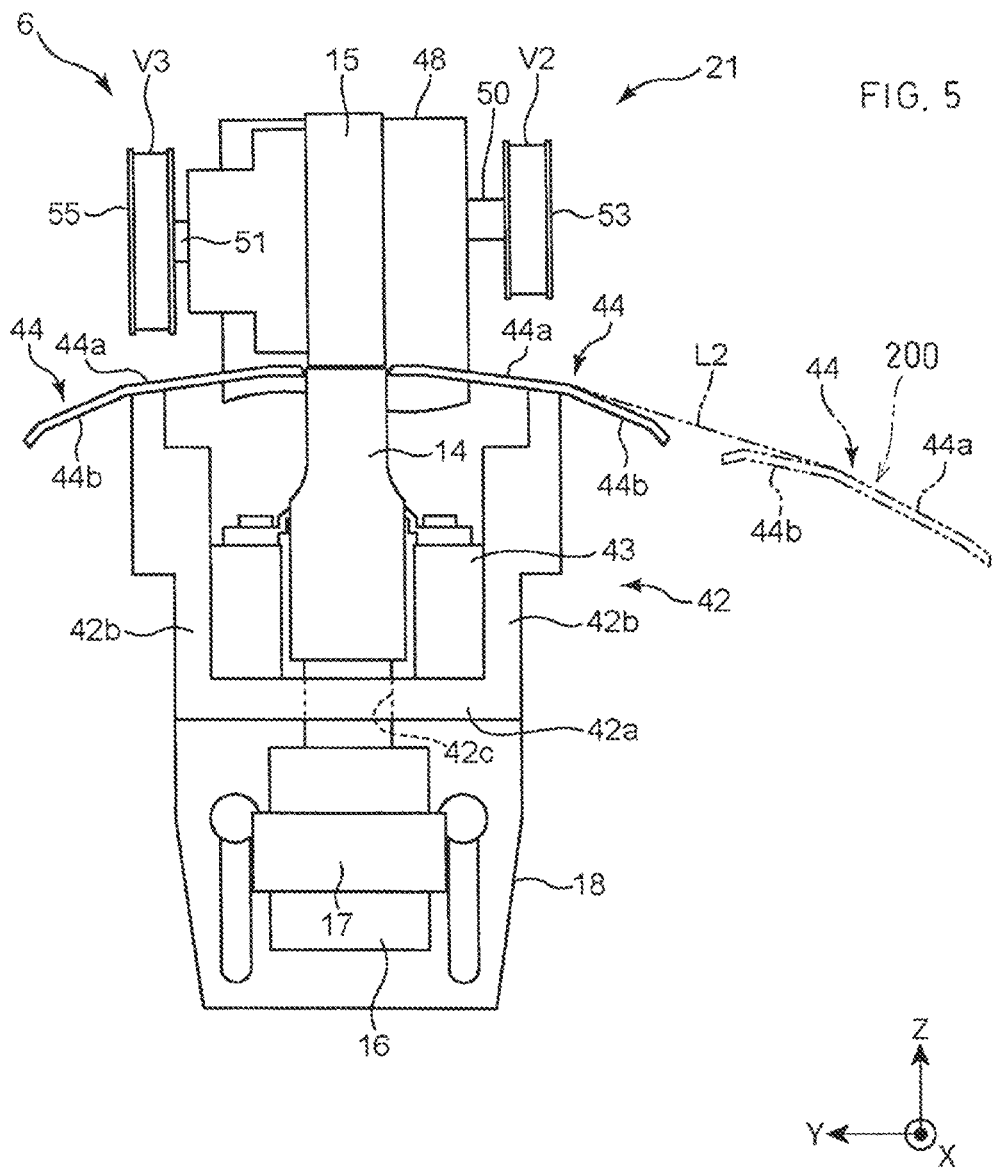
FIG. 5 is a front view showing a horn holding mechanism of FIG. 4.

Referring to FIG. 4 and FIG. 5, the horn holding mechanism 20 holds the horn 14 in an open position with the horn 14 facing outward in the radial direction.

Specifically, the horn holding mechanism 20 includes a covering member 42 that covers the horn 14 from one side in the radial direction (the lower side in FIG. 4 and FIG. 5) and from both sides in the Y direction, a horn support member 43 that supports the horn 14 inside the covering member 42, and a pair of web support members (welded portion support members) 44 fixed to the covering member 42.

The covering member 42 includes a bottom plate 42*a* and a pair of side plates 42*b* provided upright on opposite end portions of the bottom plate 42*a* in the Y direction. An insertion hole 42*c* extending in the Z direction is formed in the bottom plate 42*a*. The ultrasonic wave generator 16 arranged on the inner side in the radial direction of the covered member 42 is connected to the horn 14 through the insertion hole 42*c*.

The horn support member 43 is fixed to the covering member 42 and supports a middle portion of the horn 14 (a portion thereof that corresponds to a node of vibration from the ultrasonic wave generator 16). Note that the width dimension in the X direction corresponds to the width of the welding range D1 of the welded portion S formed on the web W (see FIG. 1).

The web support members 44 are attached to the end faces of the side plates 42*b* so as to extend in the circumferential direction about the axis L1 on both sides of the tip of the horn 14. Specifically, each web support member 44 includes a support portion 44*a* (the outer circumferential surface 44*a*) extending from the horn 14 in the circumferential direction, and a bent portion 44*b* that is bent from the end portion in the circumferential direction. Note that the disc 5*a*, the adjustment plate 5*c*, the attachment portion 18 and the web support member 44 of the rotating drum 5 correspond to a rotating support mechanism that is capable of rotating about the axis L1 and capable of supporting the continuously supplied web W on the circumference about the axis L1.

The outer circumferential surface 44*a* in the radial direction of the web support member 44 serves as a support surface for supporting the web W. Specifically, the width dimension in the x-direction of the outer circumferential surface 44*a* corresponds to the width dimension D2 (see FIG. 1) between the end portion of the web W on the waist side and the end portion of the web Won the crotch side.

As shown in FIG. 5, the bent portion 44*b* is bent from the support portion 44*a* so that the bent portion 44*b* is located on the side of the axis L1 (FIG. 4) relative to the straight line L2 that connects together the distal portions of the support portions 44*a* adjacent to each other between two horns 14.

Thus, a portion of the web W (see FIG. 1) that includes the welded portion S can be supported by the support portion 44*a* and the tip of the horn 14, and a portion of the web W that includes the absorbent body Ab thicker than the welded portion S can be arranged between bent portions 44*b* adjacent to each other. Therefore, as opposed to cases where the web W is supported on the same surface, it is possible to suppress the lifting of portions of the web W other than the absorbent body Ab due to the thickness of the absorbent body Ab.

Referring to FIG. 4 to FIG. 7, the anvil holding mechanism 21 holds the anvil 15 so that the anvil 15 can move in the X direction relative to the horn holding mechanism 20 (the horn 14).

Figure 6:
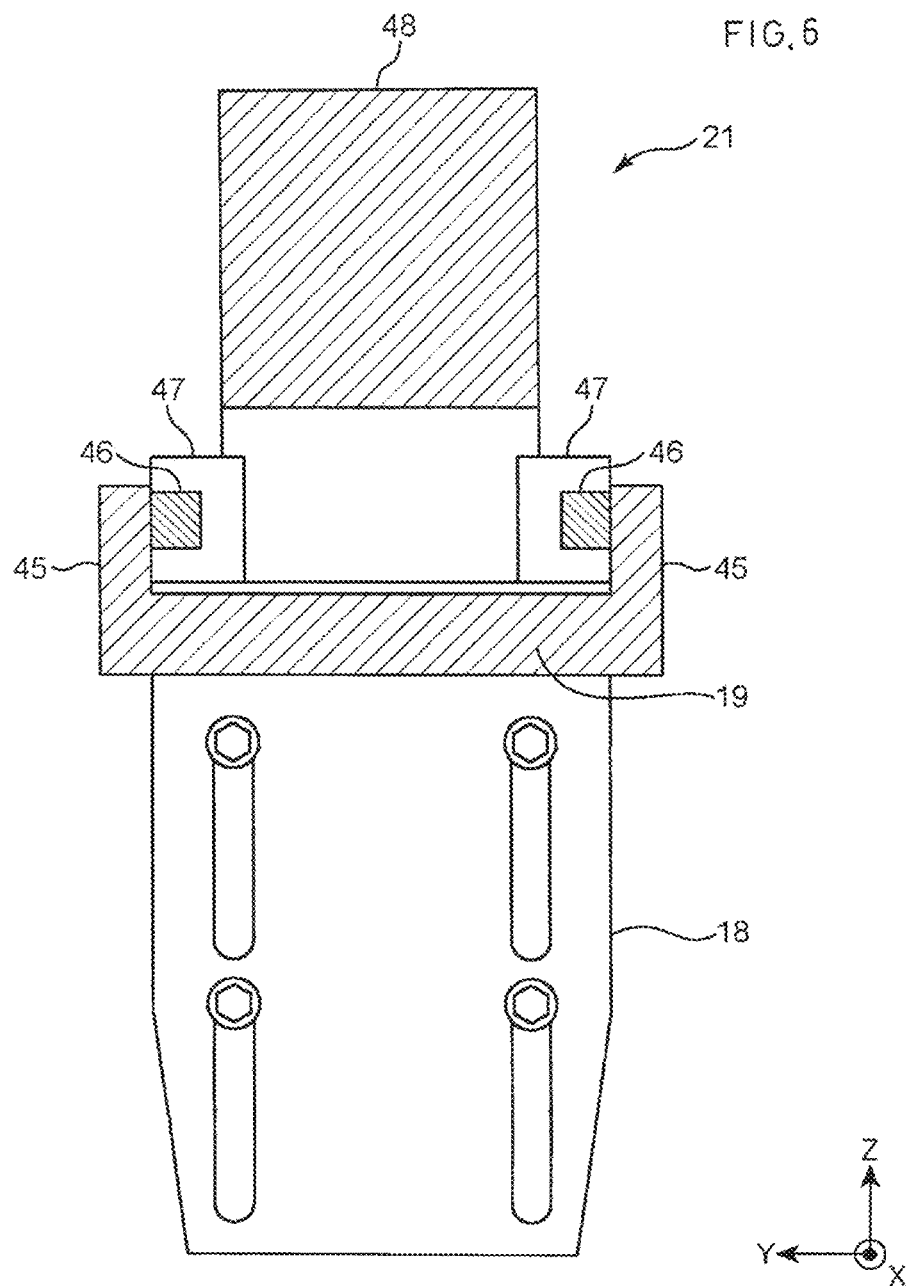
FIG. 6 is a cross-sectional view taken along line VI-VI of FIG. 4.

Specifically, as shown in FIG. 6 and FIG. 7, the anvil holding mechanism 21 includes: a pair of rail holding plates 45 provided upright on the base 19 and facing each other in the Y direction; a pair of rails 46 that are held respectively by the rail holding plates 45; a pair of sliders 47 that engage respectively with the rails 46 so that a sliders 47 can move in the X direction; a body portion 48 to which a sliders 47 are fixed; three rotating shafts 49 to 51 provided on the body portion 48; four timing pulleys 52 to 55 that can rotate about the rotating shafts 49 to 51; timing belts V2, V3 wound around the timing pulleys 52 to 55; and a link member (see FIG. 4) 59 that links together the timing belt V2 and the rail holding plate 45.

The body portion 48 is attached to the rail holding plate 45 (the base 19) so that the body portion 48 can move in the X direction by the engagement between the rails 46 and the sliders 47.

As shown in FIG. 7, the rotating shafts 49 to 51 extend in the Y direction to be next to each other in the X direction, and are capable of rotating relative to the body portion 48 about axes extending in the Y direction. The timing pulley 52 is provided at one end of the rotating shaft 49. The timing pulley 53 is provided at the end of the rotating shaft 50 on the same side as the timing pulley 52, and the timing pulley 54 is provided at the end of the rotating shaft 50 on the opposite side to the timing pulley 53. The timing pulley 55 is provided at the end of the rotating shaft 51 on the same side as the timing pulley 54, and the anvil 15 is provided at the end of the rotating shaft 51 on the opposite side to the timing pulley 55.

The timing belt V2 is wound around the timing pulley 52 and the timing pulley 53. The timing belt V3 is wound around the timing pulley 54 and the timing pulley 55. The link member 59 links together the rail holding plate 45 and a part of the timing belt V2 that is located on the axis L1 side with respect to the timing pulleys 52, 53.

When the body portion 48 moves in the X direction relative to the rail holding plate 45 (the base 19), a force is transmitted from the rail holding plate 45 through the link member 59 to move the timing belt V2 in the X direction. This causes the timing pulleys 52, 53 to rotate, and the timing pulley 54 rotates as the timing pulley 53 rotates. As a result, the movement of the timing belt V3 causes timing pulley 55 to rotate, which in turn causes the anvil 15 to rotate.

Details of the structure of the ultrasonic welding device as described above are disclosed in US 2017/0027762 A1, the entire disclosure of which is hereby incorporated by reference.

Here, the relationship between the rotational position of the anvil 15 about the axis L1 in FIG. 3 and the linear position is set by the cam groove 3a as follows, for example.

In the range (the first section) from the rotational position R0 to the rotational position R1 of FIG. 8, the anvil 15 accelerates from the origin position (FIG. 9) of the linear motion toward the stroke end (FIG. 10) (hereinafter this direction is called forward).

In the range (the second section) from the rotational position R1 to the rotational position R2, the anvil 15 moves at a constant velocity (the first velocity V1) in the forward direction. During this movement, the web W is welded between the horn 14 and the anvil 15.

In the range (the third section) from the rotational position R2 to the rotational position R3, the anvil 15 decelerates (giving backward acceleration to the anvil 15) to stop at the stroke end (FIG. 10) at the rotational position R3.

In this example, the web W is not welded during the movement in which the anvil 15 returns from the rotational position R2 to the original rotational position R0.

In the range (the fourth section) from the rotational position R3 to the rotational position R4, the anvil 15 accelerates backward from the stroke end toward the origin position.

In the range (the fifth section) from the rotational position R4 to the rotational position R5, the anvil 15 moves backward at a constant velocity (the second velocity V2).

In the range (the sixth section) from the rotational position R5 to the rotational position R0, the anvil 15 decelerates (giving forward acceleration to the anvil 15, so that the anvil 15 stops at the origin position at the rotational position R0.

The circumferential rotation of the conveying drum 200 of FIG. 2 is at a constant velocity, and thus the welding unit 6 including the anvils and the horns also rotates at a constant circumferential velocity together with the conveying drum 200.

Figure 8:
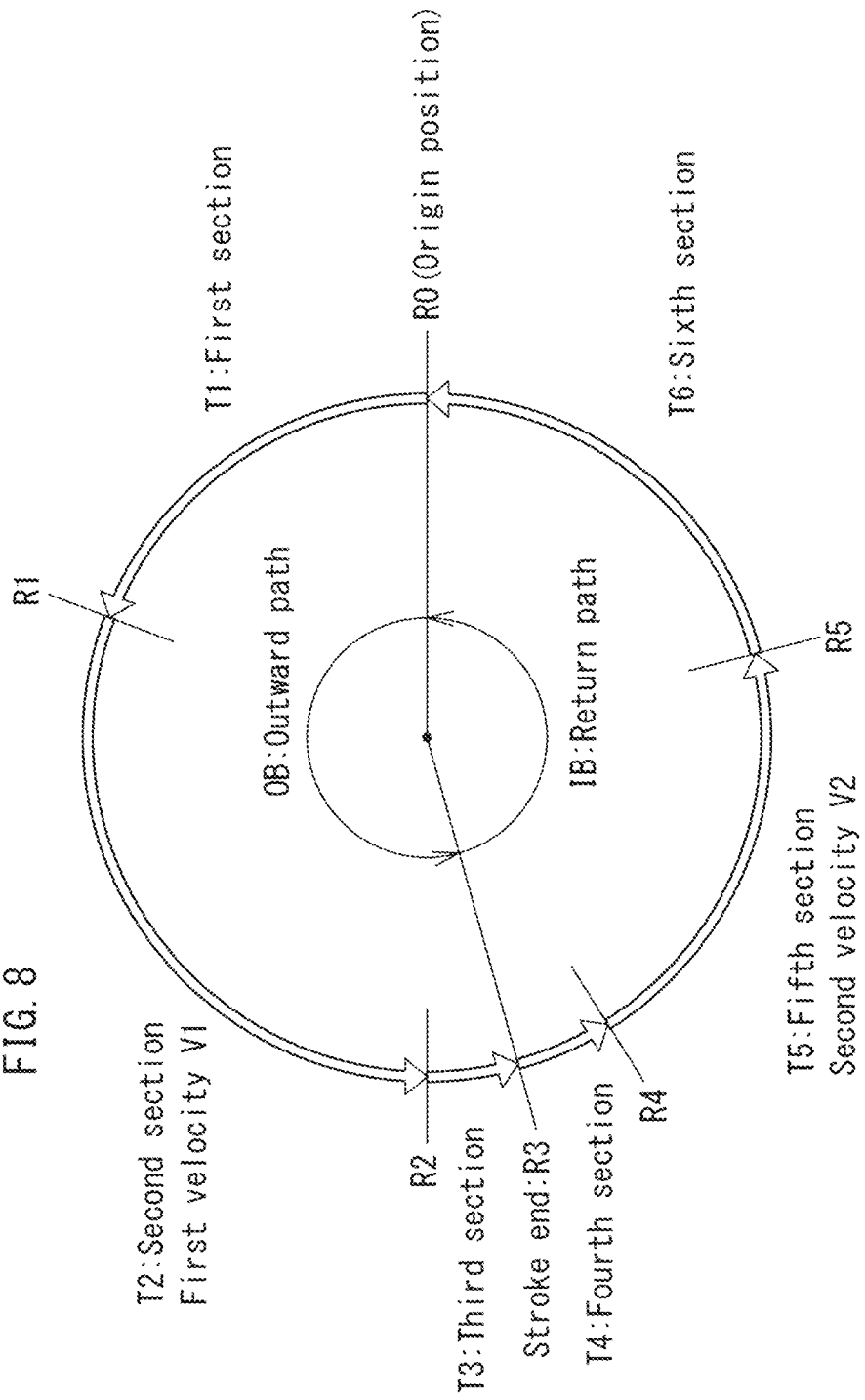
FIG. 8 is a schematic diagram showing the relationship between a rotational position and a linear position of an anvil.

On the other hand, as shown in FIG. 8, the first to third sections T1 to T3, which correspond to the outward path OB, are longer in distance than the fourth to sixth sections T4 to T6, which correspond to the return path IB.

In this example, the first velocity V1 of the anvil 15 in the second section T2 where welding is performed is smaller than the second velocity V2 of the anvil 15 in the fifth section T5 where welding is not performed. Therefore, the welding strength is stable even if welding is performed only in the outward path.

On the other hand, in this example, the second velocity V2 is greater than the first velocity V1, and the average moving velocity of the anvil 15 in the return path IB is greater than the average moving velocity of the anvil 15 in the outward path OB. Therefore, the amount of time taken for the anvil 15 to move from the origin position to the stroke end and back again to the origin position is not long.

Note that in this example, the moving mechanism 300 is configured so that the average moving velocity of the anvil 15 in the outward path OB, where the ultrasonic energy is applied, is less than that in the return path.

Thus, the difference in velocity of the anvil is obtained by asymmetrically forming the cam groove 3a of FIG. 3 so that the cam (follower) 23 of FIG. 3 is at the position of one end in the axial direction of the cam drum when at the rotational position R0 (the origin position) of FIG. 8 and is at the position of the other end in the axial direction of the cam drum when at the rotational position R3 (the stroke end) of FIG. 8.

Note that while the control unit 500 controls the ultrasonic wave generator 16 so as to perform welding only in the outward path in this example, the control unit 500 may have different modes of control so as to perform welding only in the return path or both in the outward path and in the return path.

Next, the outline of an example of the ultrasonic welding method of the present invention will be described.

As shown in FIG. 2, the web W is conveyed in the circumferential direction by the conveying drum 200.

Figure 9:
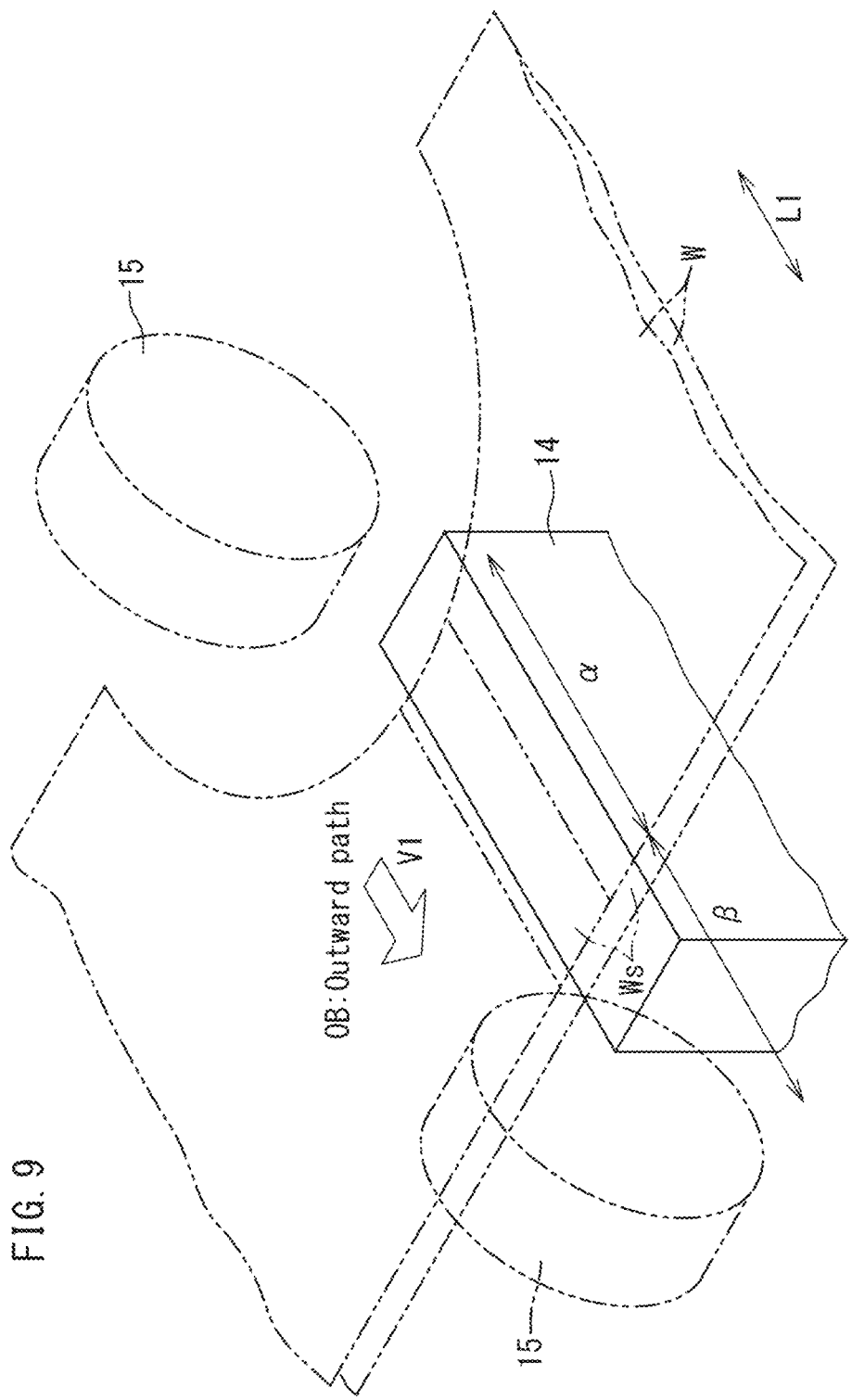
FIG. 9 is a schematic perspective view showing a linear motion of the anvil in the outward path.
Figure 10:
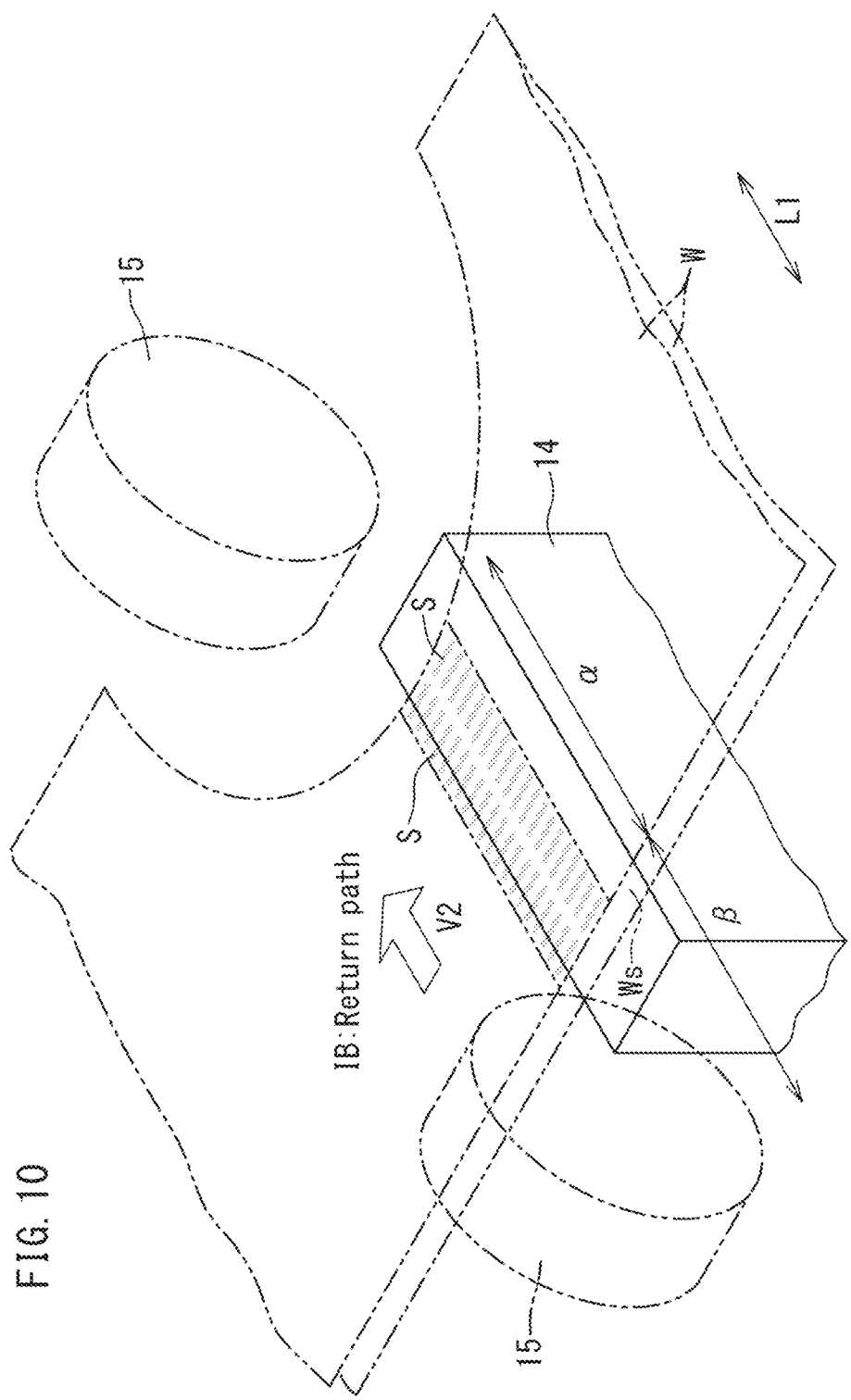
FIG. 10 is a schematic perspective view showing a linear motion of the anvil in the return path.

As the conveying drum 200 rotates, the anvil 15 reciprocates in the axis L1 direction of the conveying drum 200 as shown in FIG. 9 and FIG. 10.

During the reciprocation of the anvil 15 through the outward path OB (FIG. 9) and the return path IB (FIG. 10), the web W is held between the anvil 15 and the horn 14.

Ultrasonic energy is applied to the web W sandwiched between the anvil 15 and the horn 14 by vibrating the horn 14 of FIG. 9. The horn 14 vibrates, for example, in a direction that intersects with the surface Ws of the web W.

In this example, the anvil 15 moves at the first velocity V1 over the welding area α, which corresponds to the second section of the outward path OB, in which the anvil 15 of FIG. 9 moves straight from the origin position to the stroke end.

In the welding area α, the control unit 500 (FIG. 3) vibrates the horn 14 via the ultrasonic wave generator 16 to apply ultrasonic energy to the web W held between the anvil 15 and the horn 14 to form the welded portion S on the web W as shown in gray in FIG. 10.

In this example, the anvil 15 is moved to overrun beyond the welding area α of the web W, and a control may be performed so as not to vibrate the horn 14 in the overrun area β.

On the other hand, the settings may be such that the horn. 14 vibrates not only in the welding area α, but also immediately before entering and immediately after exiting the welding area α, in preparation for cases where the web W is displaced in a direction that intersects with the conveyance direction (the axis L1 direction).

In the return path IB in which the anvil 15 of FIG. 10 returns from the stroke end to the origin position, the control unit 500 controls the ultrasonic wave generator 16 so as not to apply ultrasonic energy to the web W.

The horn 14 may be controlled not to vibrate when not applying ultrasonic energy to the web W.

In this example, the average moving velocity of the anvil in the outward path OB is less than the average moving velocity of the anvil 15 in the return path IB. In particular, the moving velocity of the anvil 15 passing through the welding area α in the outward path OB is less than the moving velocity of the anvil 15 passing through the welding area α in the return path IB.

In the welding area α, the amplitude of the ultrasonic wave, the pressing force of the horn 14 and the anvil 15 against the web W, the moving velocity of the anvil 15, the welding area per unit area and the number of welding surfaces may be changed as needed.

While preferred embodiments have been described above with reference to the drawings, obvious variations and modifications will readily occur to those skilled in the art upon reading the present specification.

For example, the anvil may be arranged on the inner side in the radial direction of the outer circumferential surface of the web support member, and the horn may be arranged on the outer side of the outer circumferential surface.

Only one set of a horn and an anvil may be provided, or multiple sets may be provided, on the drum.

Portions of a pants-type worn article other than the so-called side seals may be welded.

Thus, such variations and modifications shall fall within the scope of the present invention as defined by the appended claims.

INDUSTRIAL APPLICABILITY

The present invention can be used in production equipment for disposable worn articles such as disposable pants, diapers, sanitary products, etc., as well as in production equipment for wound dressing materials for medical use, etc.

REFERENCE SIGNS LIST

1: Ultrasonic welding device, 2 Drive shaft support member, 2a: Through hole, 3: Cam drum, 3a: Cam groove, 4: Drive shaft, 4a: Pulley, 5: Rotating drum, 5a: Disc, 5b: Covering wall, 5c: Adjustment plate, 5e: Screw hole, 6: Welding unit, 7: Power transmission mechanism, 8: Slip ring, 9: Rotary joint
10: Motor, 10a: Pulley, 11: Wire guide member, 12: Pipe connection member, 14: Horn, 15: Anvil, 16: Ultrasonic wave generator, 17: Cooling jacket, 18: Attachment portion, 19: Base
20: Horn holding mechanism, 21: Anvil holding mechanism, 23: Cam follower
42: Covering member, 42a: Bottom plate, 42b: Side plate, 42c: Through hole, 43: Horn holding member, 44: Web support member, 44a: Outer circumferential surface, 44b: Bent portion, 45: Rail holding plate, 46: Rail, 47: Slider, 48: Body portion, 49 to 51: Rotating shaft
52 to 55: Timing pulley, 59: Link member
70: Disposable diaper, 70a: Front abdomen portion, 70b: Rear back portion, 70c: Crotch portion
200: Conveying drum
300: Moving mechanism
500: Control unit
Ab: Absorbent body, D1: Welding range, D2: Width dimension, F1: Inlet roller, F2: Outlet roller, L: Leg hole, L1: Axis, L2: Straight line, S: Welded portion
OB: Outward path, IB: Return path
P1: Conveying step, P2: Leg hole formation step, P3: Absorbent body attachment step, P4: Two-fold step, P5: Welding step, P6: Cut-off step
V1: Belt, V2, V3: Timing belt, W: Web, Ws: Surface of web
α: Welding area, β: Overrun area

The invention claimed is:

1. An ultrasonic welding method of welding a web by means of an ultrasonic welding device, the ultrasonic welding device comprising:
a conveying drum that conveys the web along an outer circumferential surface while rotating;
at least one horn that is arranged on one of an inner side and an outer side in a radial direction of the conveying drum relative to the outer circumferential surface, the horn rotating together with the conveying drum; and
at least one anvil that is arranged on another one of the inner side and the outer side in the radial direction of the conveying drum relative to the outer circumferential surface, the anvil rotating together with the conveying drum; the ultrasonic welding method comprising:
a step of conveying the web by the conveying drum;
a step of reciprocating the anvil in an axis direction of the conveying drum as the conveying drum rotates so as to hold the web between the anvil and the horn in an outward path and a return path of the anvil;
a step of vibrating the horn to apply ultrasonic energy to the web sandwiched between the anvil and the horn; and
a step of controlling vibration of the horn via an ultrasonic wave generator of the ultrasonic welding device so as to apply ultrasonic energy to the web in one of the outward path and the return path and not to apply ultrasonic energy to the web in another one of the outward path and the return path,
wherein in the step of reciprocating the anvil, the anvil moves so as to overrun beyond a welding area where the web should be welded and the horn is not vibrated in the overrun area,
wherein in the step of reciprocating the anvil, the anvil moves at a constant velocity when the anvil moves the welding area and starts to decelerate when the anvil has passed the welding area, and
wherein the anvil reciprocates so that an average moving velocity of the anvil in the one of the outward path and the return path in which ultrasonic energy is applied is smaller than an average moving velocity of the anvil in the other one of the outward path and the return path.

2. The ultrasonic welding method according to claim 1, wherein a control is performed so as not to vibrate the horn when ultrasonic energy is not applied to the web.

3. An ultrasonic welding device, comprising:
a conveying drum configured to convey a web along an outer circumferential surface while rotating;
at least one horn that is arranged on one of an inner side and an outer side in a radial direction of the conveying drum relative to the outer circumferential surface, the horn being configured to rotate together with the conveying drum;
at least one anvil that is arranged on another one of the inner side and the outer side in the radial direction of the conveying drum relative to the outer circumferential surface, the anvil being configured to rotate together with the conveying drum;
a moving mechanism configured to reciprocate the anvil in an axis direction of the conveying drum as the conveying drum rotates so as to hold the web between the anvil and the horn in an outward path and a return path of the anvil;
an ultrasonic wave generator configured to vibrate the horn to apply ultrasonic energy to the web sandwiched between the anvil and the horn; and
a control unit configured to perform a control of vibrating the horn via the ultrasonic wave generator so as to apply ultrasonic energy to the web in one of the outward path and the return path and not to apply ultrasonic energy to the web in another one of the outward path and the return path,
wherein the moving mechanism is configured so that the anvil overruns beyond a welding area where the web should be welded to an overrun area,
wherein the control unit is configured to perform a control so that the ultrasonic wave generator does not vibrate the horn in the overrun area,
wherein the moving mechanism is configured to move the anvil at a constant velocity when the anvil moves the welding area and to start to decelerate the anvil when the anvil has passed the welding area, and wherein the moving mechanism is configured so that an average moving velocity of the anvil in the one of the outward path and the return path in which ultrasonic energy is applied is smaller than an average moving velocity of the anvil in the other one of the outward path and the return path.

4. The ultrasonic welding device according to claim 3, wherein the control unit is configured to control the ultrasonic wave generator so as not to vibrate the horn when ultrasonic energy is not applied to the web.

* * * * *